United States Patent [19]
Wijay

[11] Patent Number: 5,690,643
[45] Date of Patent: Nov. 25, 1997

[54] STENT DELIVERY SYSTEM

[75] Inventor: Bandula Wijay, Friendswood, Tex.

[73] Assignee: Leocor, Incorporated, Houston, Tex.

[21] Appl. No.: 603,267

[22] Filed: Feb. 20, 1996

[51] Int. Cl.[6] ........................................... A61F 11/00
[52] U.S. Cl. ............................. 606/108; 606/198
[58] Field of Search .................................. 606/108, 191, 606/198, 194, 170

[56] References Cited

U.S. PATENT DOCUMENTS

| Re. 34,037 | 8/1992 | Innue et al. |
|---|---|---|
| 2,701,559 | 2/1955 | Cooper. |
| 3,882,845 | 5/1975 | Bucalo. |
| 3,889,685 | 6/1975 | Miller, Jr. et al. |
| 4,018,230 | 4/1977 | Ochiai et al. |
| 4,183,102 | 1/1980 | Guiset. |
| 4,483,340 | 11/1984 | Forgarty et al. |
| 4,503,569 | 3/1985 | Dotter. |
| 4,732,152 | 3/1988 | Wallsten et al. |
| 4,740,207 | 4/1988 | Kreamer. |

(List continued on next page.)

FOREIGN PATENT DOCUMENTS

| 0 183 372 A1 | 4/1986 | European Pat. Off. |
| 0 621 017 A1 | 10/1994 | European Pat. Off. |
| 2 135 585 A | 11/1983 | WIPO. |

OTHER PUBLICATIONS

D. Maass, et al., Radiological Follow-up of Transluminally Inserted Vascular Endoprostheses: An Experimental Study Using Expanding Spirals, Surigical Clinic A and the Department of Radiology, University Hospital Zurich, Switzerland, Sep. 1983, 5 pages.

Charles T. Dotter, M.D., Transluminally-placed Coilspring Endarterial Tube Grafts, Long-Term Patency in Canine Popliteal Artery, Investigative Radiology, Sep.-Oct., 1969, 3 pages.

Andrew Cragg, M.D., et al., Nonsurgical Placement of Arterial Endoprostheses: A New Technique Using Nitinol Wire, Department of Radiology, University of Minneapolis, MN, Nov., 1982, 4 pages.

Kenneth C. Wright, Ph.D., et al., Percutaneous Endovascular Stents: An Experimental Evaluation, Department of Radiological Sciences, University of Texas at Houston, M.D. Anderson Hospital and Tumor Institute, Houston, Texas, Sep., 1984, 3 pages.

Julio C. Palmaz, M.D., et al., Expandable Intraluminal Graft: A Preliminary Study, Department of Radiology and Pathology, University of Texas Health Science Center at San Antonio and Memorial Medical Center, Corpus Christy, Texas, 1 page.

Charles T. Dotter, et al., Transluminal Expandable Nitinol Coil Stent Grafting: Preliminary Report, William A. Cook Research Labortory, Departemnt of Diagnostic Radiology, School of Medicine, Oregon Health Sciences University, Portland Oregon, 1982, 2 pages.

*Primary Examiner*—Michael Buiz
*Assistant Examiner*—Kevin Truong
*Attorney, Agent, or Firm*—Rosenblatt & Redano P.C.

[57] ABSTRACT

A stent delivery apparatus is disclosed comprising a movable inner tube and a fixed outer tube having corrugations or undulations at its distal end. The undulations or corrugations are stretched by movement of the inner tube, whereupon the stent is placed over the relatively flattened undulations or corrugations. A solid structure or an open structure such as a coil can be used for this purpose. One large proximal undulation is provided for preventing the stent from sliding from the predetermined location during the setting. Upon relative movement between the inner and outer tubes, which can be a single longitudinal or twisting movement or a combination of such movements, the undulations under the stent are outwardly relaxed, forcing the stent to expand toward the vascular wall. The relative movement is then reversed to retract the undulations and the delivery device withdrawn. In an alternative embodiment, the undulations are perforated to allow perfusion under and through the stent from a point external to the patient's body to a point distal of the placement of the stent during the procedure of stent expansion.

23 Claims, 5 Drawing Sheets

U.S. PATENT DOCUMENTS

| | | |
|---|---|---|
| 4,776,337 | 10/1988 | Palmaz . |
| 4,795,458 | 1/1989 | Regan . |
| 4,886,062 | 12/1989 | Wiktor . |
| 4,913,141 | 4/1990 | Hillstead . |
| 4,950,227 | 8/1990 | Savin et al. . |
| 4,964,853 | 10/1990 | Bugiyama et al. . |
| 4,990,151 | 2/1991 | Wallsten . |
| 5,074,871 | 12/1991 | Groshong .................... 606/198 |
| 5,100,429 | 3/1992 | Sinofsky et al. . |
| 5,108,416 | 4/1992 | Ryan et al. . |
| 5,135,536 | 8/1992 | Hillstead . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froiz . |
| 5,163,958 | 11/1992 | Pinchuk . |
| 5,197,978 | 3/1993 | Hess . |
| 5,282,824 | 2/1994 | Gianturco . |
| 5,354,310 | 10/1994 | Garnic et al. .................... 606/198 |
| 5,415,637 | 5/1995 | Khosravi .................... 606/198 |
| 5,423,885 | 6/1995 | Williams . |
| 5,439,445 | 8/1995 | Kontos . |
| 5,443,500 | 8/1995 | Sigwart . |
| 5,456,667 | 10/1995 | Ham et al. .................... 606/198 |
| 5,480,423 | 1/1996 | Ravenscroft et al. . |

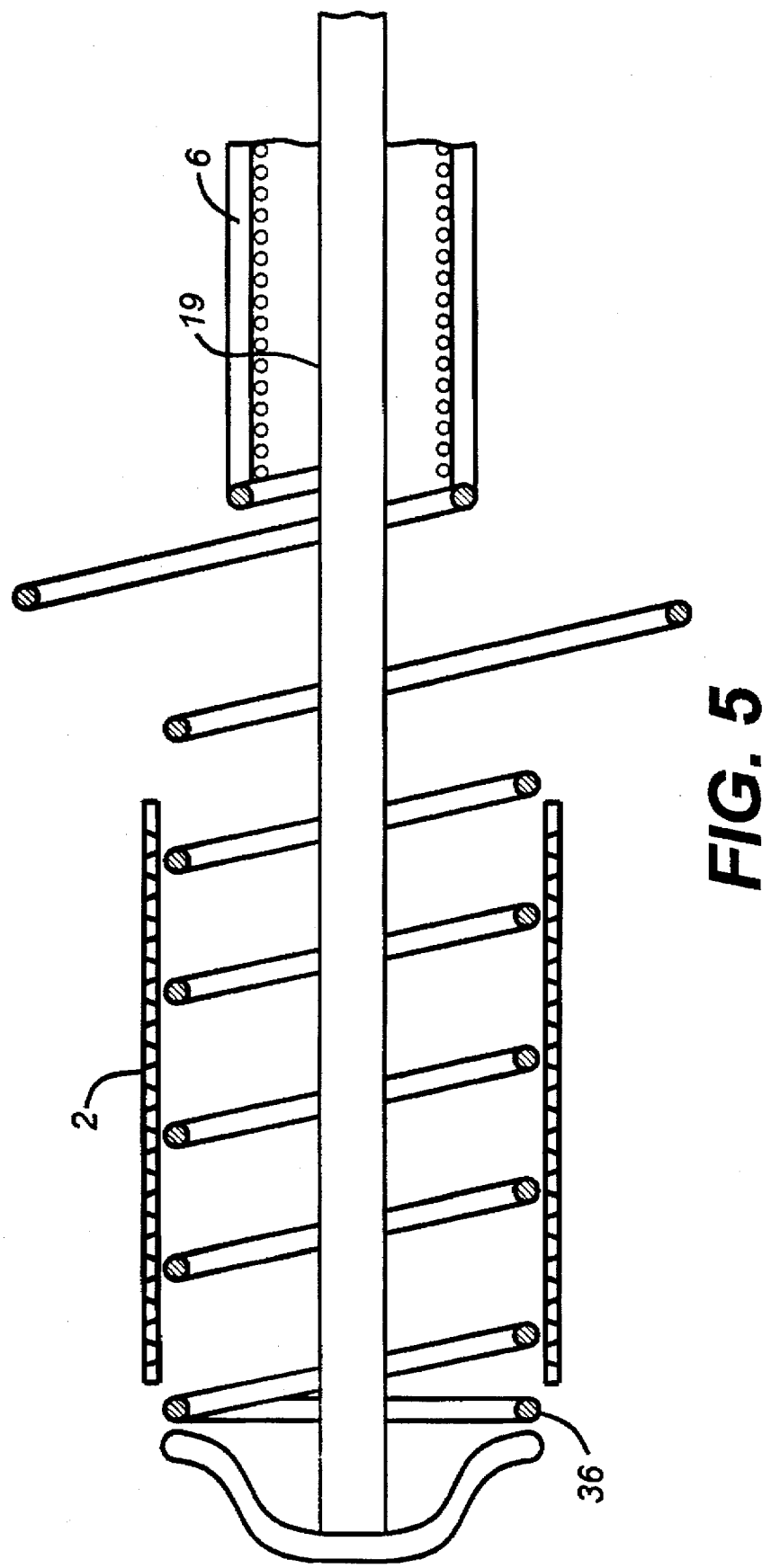

STENT DELIVERY SYSTEM

FIELD OF THE INVENTION

The field of this invention relates to techniques for delivery and placement of stents in the vascular system.

BACKGROUND OF THE INVENTION

Stents have been in popular use for some time and have taken many different configurations. Generally, stents are tubular structures which are delivered to a desired location in the vascular system and set in place to hold open the vessels which are narrowed or occluded by disease. There have been several types of stents employed in the past. Some are coiled and retained in the coiled position until properly placed, at which point a sheath or retainer is removed and the stent is allowed to uncoil against the vessel wall. Typical of such stents are U.S. Pat. Nos. 5,423,885; 5,439,445; 5,443,500; and European application 0621017A1.

Other stents are expandable and have generally in the past been delivered and expanded using balloon catheters. One such stent and delivery technique therefore are illustrated in U.S. Pat. Nos. 4,776,337 and 4,886,062.

The object of the apparatus of the present invention is to provide a delivery technique which allows for predictable and measurable degrees of expansion of the stent, once properly located. Additionally, another object is to allow for perfusion during the expansion procedure, thus preventing discomfort to the patient from cut-off in circulation, which occurs during balloon inflation when using the prior techniques, such as in U.S. Pat. No. 4,776,337, to expand the stent by balloon inflation. It is another object to allow the doctor to have controls which give an idea of the level of expansion that has taken place proportional to movement of a slide or equivalent device by the doctor during the procedure.

SUMMARY OF THE INVENTION

A stent delivery apparatus is disclosed comprising a movable inner tube and a fixed outer tube having corrugations or undulations at its distal end. The undulations or corrugations are stretched by movement of the inner tube, whereupon the stent is placed over the relatively flattened undulations or corrugations. A solid structure or an open structure such as a coil can be used for this purpose. One large proximal undulation is provided for preventing the stent from sliding from the predetermined location during the setting. Upon relative movement between the inner and outer tubes, which can be a single longitudinal or twisting movement or a combination of such movements, the undulations under the stent are outwardly relaxed, forcing the stent to expand toward the vascular wall. The relative movement is then reversed to retract the undulations and the delivery device withdrawn. In an alternative embodiment, the undulations are perforated to allow perfusion under and through the stent from a point external to the patient's body to a point distal of the placement of the stent during the procedure of stent expansion.

BRIEF DESCRIPTION OF THE DRAWINGS

FIG. 5 shows an alternative embodiment using a spring which is expanded to place the stent using rotational movement.

DETAILED DESCRIPTION OF THE PREFERRED EMBODIMENT

Figure 1:
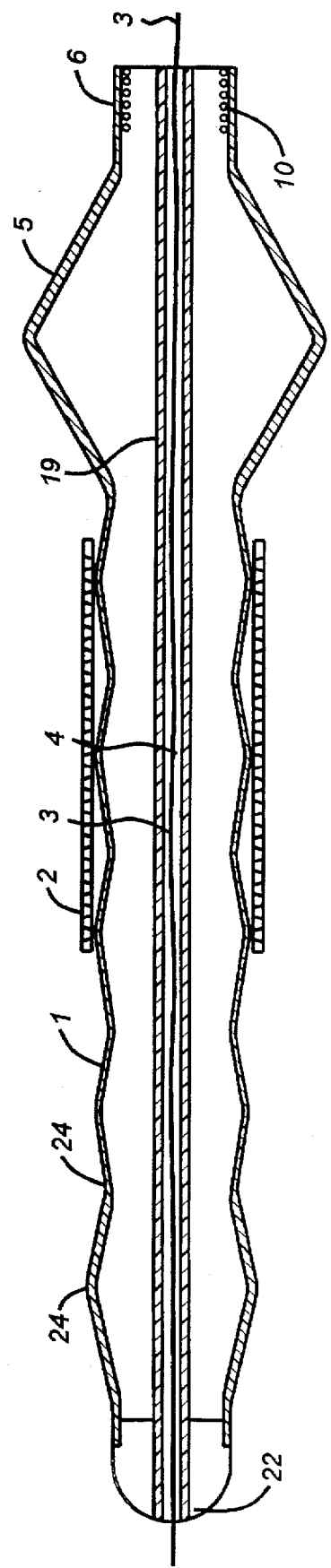
FIG. 1 is a sectional elevational view of the stent delivery apparatus with the stent in position prior to running into the body.
Figure 2:
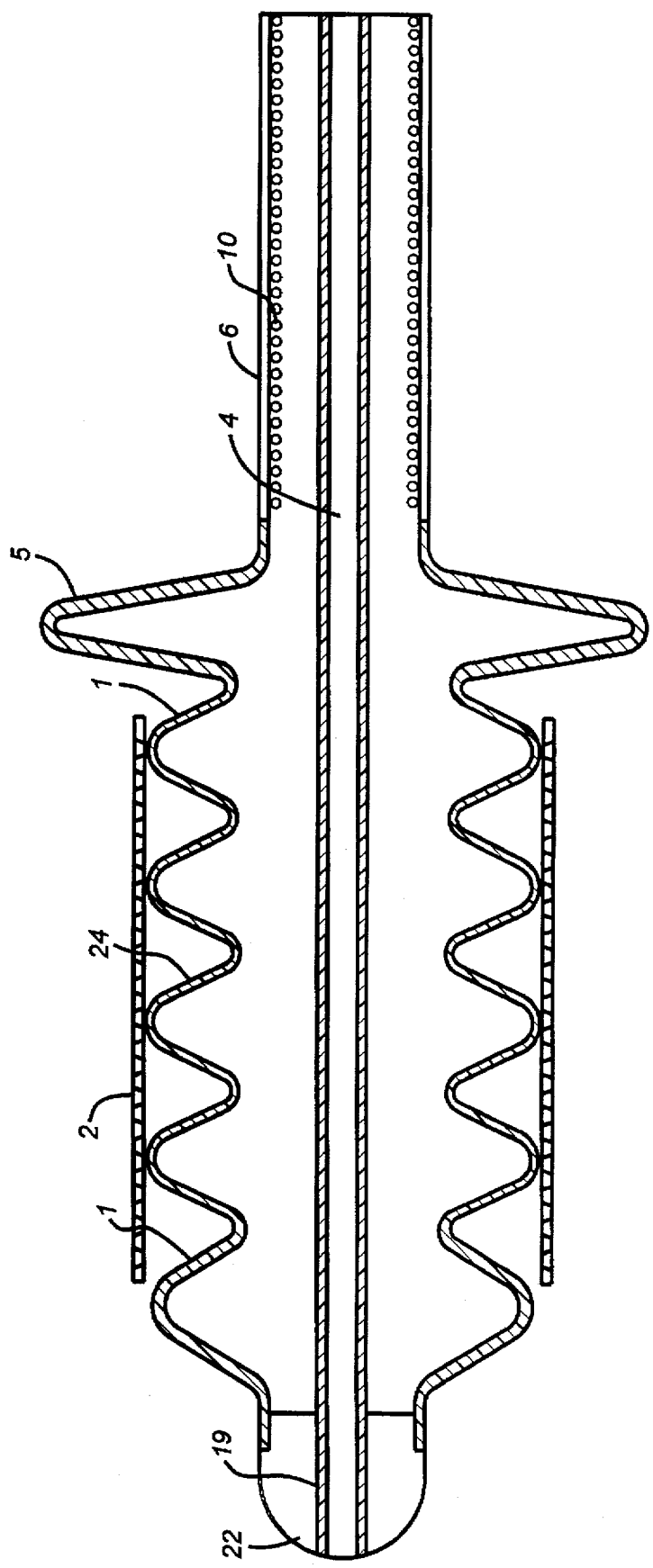
FIG. 2 is the device of FIG. 1, with the stent shown in an expanded state caused by relative movement between the inner and outer tubes of the delivery apparatus.
Figure 4:
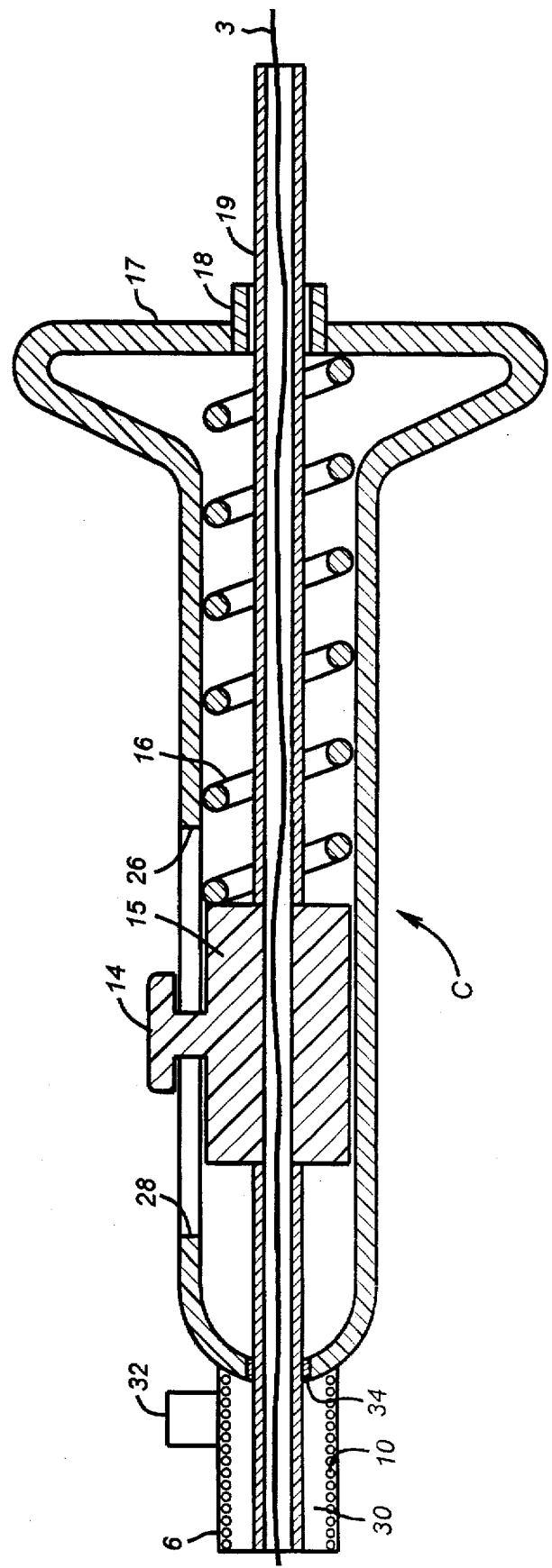
FIG. 4 is the proximal end of the stent delivery apparatus which is operated by the doctor during the procedure so as to cause relative movement between the inner and outer tubes.

One embodiment of the present invention can be seen in FIGS. 1, 2, and 4. An inner tube 19 extends from the proximal end 20 (see FIG. 4) to a distal end 22. Tube 19 has a lumen 4 internally which accepts a guidewire 3. Attached to the distal end 22 is a flexible segment 1, which is made up of a plurality of undulations or bends 24 and is shown in FIG. 1 in the small-diameter position as a result of relative movement between the outer tube 6 and the inner tube 19. While a wall structure, preferably made of nylon, polyurethane, polyethylene, spring steel, or phospo bronze, can be used, a coil, preferably made of nickel-titanium alloys, stainless steel, spring steel, or phospho bronze, can also be used without departing from the spirit of the invention. When using nickel-titanium alloys having memory, it is preferable that the coil 36 is introduced in the extended condition while cold saline is passed to maintain the coil in the stretched status. When the cold saline flow is stopped and the coil 36 warms to body temperature, it assumes the previously formed status of a coil having a larger diameter, thereby expanding the stent which is carried on a thin polymeric sleeve to its highest dimension based on the final diameter of the coil 36.

The hand-held control C (see FIG. 4) is used to regulate the relative movement between the inner tube 19 and the outer tube 6. The outer tube 6 has a large bend 5. In the position shown in FIG. 1, with the bends 24 at their small-diameter orientation, the large bend 5 extends radially outwardly further for a purpose which will be described below.

The stent 2, which can be any known type of expandable stent, is inserted over the bends 24 when the bends 24 are in the position shown in FIG. 1. In that position, the stent easily slips over the bends 24. After it is positioned in the location shown in FIG. 1, a very slight relative movement between the inner tube 19 and the outer tube 6 secures the stent in the position of FIG. 1. Stated differently, the bends 24 are pulled until they are almost defining a cylindrical surface to facilitate mounting of the stent tube. The bends 24 are somewhat relaxed prior to insertion over the guidewire 3 to the point shown in FIG. 1 for advancement over the guidewire, with the stent 2 held in position by the slightly relaxed bends 24.

FIG. 4 illustrates the hand-held control C used to create the relative movement between the inner tube 19 and the outer tube 6. The control C has a handle 14. Handle 14 has travel stops 26 and 28 and is fixedly attached to the inner tube 19 for manipulation by hand of the inner tube 19 while retaining the housing 17 stationary. The inner tube 19 extends through a bushing 18, thus allowing it to translate back and forth with respect to the housing 17. The spring 16 biases the block 15. The surgeon manipulates the handle 14. The spring 16 biases the block 15 toward stop 28. Accordingly, the bias is to put the bends 24 in the position shown in FIG. 1.

To get the bends 24 into the position shown in FIG. 2, the force of the biasing spring 16 must be overcome by the doctor's fingers pulling the handle 14 back toward stop 26. When that occurs, the outer tube 6 is put in compression. Inner spring 10 preferably extends the length of the outer tube 6 to give it column strength so that it does not buckle as the inner tube 19 is pulled proximally, starting at end 22. Those skilled in the art will appreciate that when the housing 17 is used to fix the position of the outer tube 6 and the handle 14 is pulled against spring 16 toward stop 26, the distal end 22 of inner tube 19 is brought closer to the large bend 5, which in itself gets bigger radially due to this relative movement. The stent 2, which is circumscribing the bends 24, is physically expanded due to the expanding diameter of the bends 24 as the distal end 22 of inner tube 19 is pulled proximally with the outer tube 6 held stationary.

It should also be noted that there is a relationship between the amount of proximal movement of the handle 14 and the amount of radial movement of the collection of bends 24. Thus, the surgeon can know precisely how far the stent 2 has been expanded by controlling with his or her hand the amount of movement of the block 15. This should be contrasted with delivery devices, such as those described in the U.S. Pat. No. 4,776,337, which use a balloon under a stent. Those experienced in balloon catheters will know that the recommended procedure in using balloons is to expand the balloon as fast as possible. The balloon may expand to a fully inflated position, which is one point of demarcation of expansion of the stent. However, the rate of expansion to full inflation is generally recommended to be accomplished fairly quickly and, thus, no control is afforded between the onset of expansion of the stent until the balloon reaches full inflation. In the event additional inflation is required using a balloon, uncertainty is then added into the procedure since the amount or location of the growth of the balloon beyond full inflation or beyond inflation to a predetermined point is less certain.

This is to be contrasted with the apparatus described in FIGS. 1, 2, and 4 where the movement of the block 15 against spring 16 toward stop 26 brings the distal end 22 proximally while holding outer tube 6 stationary, thus allowing the bends to compress to a known degree with respect to each increment of relative axial movement between the inner tube 19 and the outer tube 6. Thus, within limits defined by comparing FIGS. 1 and 2, the stent 2 can be expanded to any interim value and that value can be known while the expansion progresses. The expansion can also be done at the rate preferred by the surgeon and can be done slowly or quickly as required.

The advantage of the large bend 5 becomes apparent as it is time to expand the stent 2. The large bend 5 comes into play as the small bends 24 are allowed to expand. The stent 2 is held in position and is prevented from moving proximally as it is being expanded when the bends 24 are growing radially. The large bend 5 acts as a travel stop against any tendency of the stent 2 to creep proximally. Ultimately, when the desired expansion of the stent 2 is reached, as shown in FIG. 2, the stent 2 retains its expanded shape against the vascular wall and the bends 24 are collapsed in the manner previously described, thus allowing the insertion apparatus to be removed from the stent. In order to release from the stent 2, the surgeon relaxes the grip on the handle 14 to allow the spring 16 to bias the block 15 toward stop 28. This returns the bends 24 back to their position shown in FIG. 1.

Figure 3:
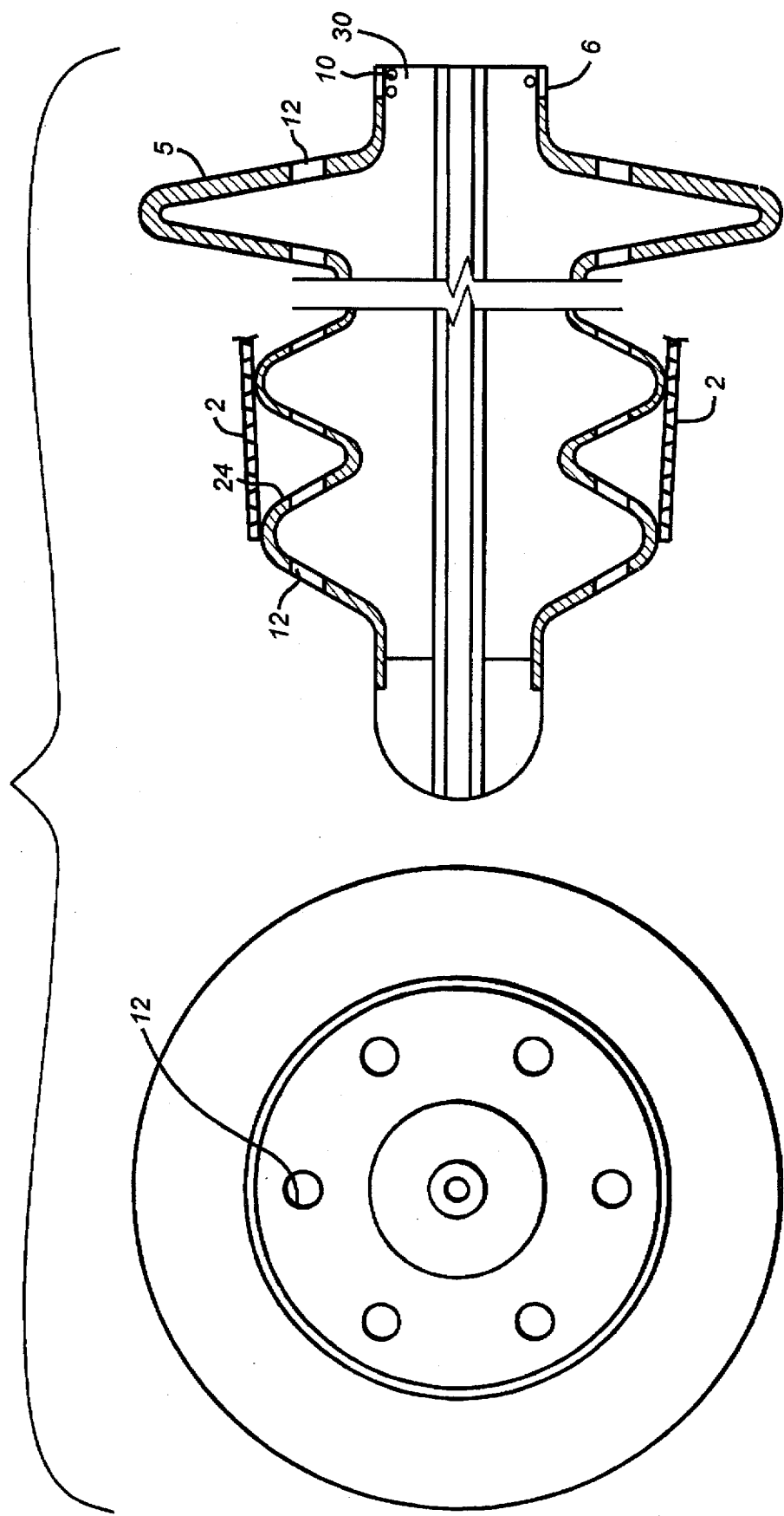
FIG. 3 is an alternative embodiment to that shown in FIGS. 1 and 2 and illustrates openings in the undulating outer tube at its distal end to promote the ability to perfuse during expansion of the stent.

FIG. 3 represents the preferred embodiment. The big difference between the design of FIGS. 1 and 2 and that of FIG. 3 is that there are perforations 12, not only in the big bend 5 but in the smaller bends 24. The advantage is that the annular space 30 can be easily fitted at the proximal end, as shown in FIG. 4, with a side connection 32 to allow the annular space 30 to carry drugs or blood while the procedure is ongoing. The drugs or blood exits through the openings 12 and thus reduces the discomfort to the patient during the setting procedure for the stent 2. The openings 12 are shown alongside in FIG. 3 as being distributed around the periphery of the bends 24, as well as the big bend 5. In all other respects, the preferred embodiment of FIG. 3 works identically to the embodiment shown in FIGS. 1 and 2.

Those skilled in the art will appreciate that minor modifications to the control shown in FIG. 4 will have to be made to allow access into the annulus 30. For example, a T-connection, shown schematically as 32, coupled with sufficient seals 34, can provide the access into the annulus 30 for perfusion of blood or drugs during the setting of the stent 2, as well as during the removal procedure from inside the stent, as described above.

Those skilled in the art will also appreciate that the apparatus described represents numerous improvements over the stent delivery systems currently available. The rate of expansion of the stent 2 can be controlled, and the amount of its expansion can be known. This is an advantage provided over prior delivery systems using a balloon. Additionally, the use of the openings 12 in the flexible segment 1 provides for the ability to perfuse under the stent 2 while it is being expanded, a feature not available if using a balloon to expand the stent 2. A provision is also included in the delivery device to prevent shifting longitudinally of the stent 2 until it is sufficiently expanded to take anchor in the surrounding vascular wall.

FIG. 5 is an alternative embodiment that uses a coil 36 to expand the stent 2. The coil 36 is contracted by a relative twisting between the inner tube 19 and the outer tube 6.

When the coil 36 is in tension, it will have a small enough diameter to fit the stent 2 over it and secure its placement until the assembly is positioned in a body. The coil 36 is then allowed to relax, which increases its diameter and expands the stent 2. Since the coil 36 is open, it permits perfusion through annulus 30, as previously described. The inner spring 10 improves the resistance of the outer tube 6 to an applied torque. It is clear that setting the stent 2 can be done with a relative longitudinal force, as shown in FIG. 2, a relative twist force, as shown in FIG. 5, or some combination of such movements. The end held by the doctor for the coil version shown in FIG. 5 is different from that shown in FIG. 4 to allow the doctor to apply a twist force to the inner tube 19.

The foregoing disclosure and description of the invention are illustrative and explanatory thereof, and various changes in the size, shape and materials, as well as in the details of the illustrated construction, may be made without departing from the spirit of the invention.

I claim:

1. A stent delivery system, comprising:
   an inner elongated member;
   an outer elongated member mounted over and movable with respect to said inner elongated member;
   a flexible member connected to said inner elongated member and said outer elongated member;
   a stent overlying said flexible member;
   said flexible member movable from a first contracted position, where said flexible member longitudinally retains said stent with respect to said elongated members for insertion, to a second expanded position, where said stent is expanded for fixation, by virtue of relative movement between said inner and outer elongated members.

2. The system of claim 1, wherein:
said relative movement is longitudinal.

3. The system of claim 2, wherein:
said outer elongated member is reinforced for column strength against a compressive applied force which results from said relative longitudinal movement.

4. The system of claim 3, wherein:
said reinforcement comprises a wound spring extending for at least a portion of the length of said outer elongated member.

5. The system of claim 2, wherein:
said inner elongated member has a tubular structure to facilitate passing it over a guidewire.

6. The system of claim 2, wherein:
said flexible member has at least one opening thereon to permit perfusion of fluids therethrough adjacent said stent while it is being expanded by said flexible member.

7. The system of claim 6, wherein:
said inner and outer elongated members forming an annulus therebetween which is in flow communication with said opening in said flexible member for allowing perfusion during expansion of said flexible member.

8. The system of claim 7, wherein:
said flexible member comprises a generally tubular structure with an undulating wall further comprising at least two reverse bends;
said contracted position defined by a small profile of said reverse bends and said expanded position defined by at least one of said reverse bends moving radially away from another said reverse bends.

9. The system of claim 1, wherein:
said relative movement is rotational.

10. The system of claim 1, wherein:
said relative movement occurs by a combination of longitudinal and rotational movement.

11. The system of claim 1, wherein:
said flexible member has at least one opening thereon to permit perfusion of fluids therethrough adjacent said stent while it is being expanded by said flexible member.

12. The system of claim 11, wherein:
said inner and outer elongated members forming an annulus therebetween which is in flow communication with said opening in said flexible member for allowing perfusion during expansion of said flexible member.

13. The system of claim 1, wherein:
said flexible member comprises a generally tubular structure with an undulating wall further comprising at least two reverse bends;
said contracted position defined by a small profile of said reverse bends and said expanded position defined by at least one of said reverse bends moving radially away from another said reverse bends.

14. The system of claim 1, wherein:
said flexible member comprises a coil;
said contracted position defined by a relative rotation between said inner and outer members which results in a small profile for said flexible member.

15. The system of claim 14, wherein:

said expanded position is defined by a larger profile for said flexible member which results from relaxation of said coil from relative rotation of said inner and said outer members.

16. A stent delivery system, comprising:
an inner elongated member;
an outer elongated member mounted over and movable with respect to said inner elongated member;
a flexible member connected to said inner elongated member and said outer elongated member;
a stent mounted to said flexible member;
said flexible member movable from a first contracted position, where said flexible member longitudinally retains said stent with respect to said elongated members for insertion, to a second expanded position, where the stent is expanded for fixation, by virtue of relative movement between said inner and outer elongated members;
said flexible member comprising a generally tubular structure with an undulating wall; and
said undulating wall further comprises an undulation which has a larger profile than said other undulations which comprise said wall, in both the contracted and expanded positions of said wall, to reduce longitudinal shifting of the stent as said wall is expanded.

17. A stent delivery system, comprising:
an inner elongated member;
an outer elongated member mounted over and movable with respect to said inner elongated member;
a flexible member connected to said inner elongated member and said outer elongated member;
a stent mounted to said flexible member;
said flexible member movable from a first contracted position, where it supports the stent for insertion, to a second expanded position, where the stent is expanded for fixation, by virtue of relative movement between said inner and outer elongated members;
said flexible member comprises a coil; and
said coil comprises at least one turn which has a larger profile than the remaining turns of said coil in its said contracted and expanded positions, to reduce longitudinal shifting of the stent as said coil is expanded.

18. A stent delivery system, comprising:
an inner elongated member;
an outer elongated member mounted over and movable with respect to said inner elongated member;
a flexible member connected to said inner elongated member and said outer elongated member;
a stent mounted to said flexible member;
said flexible member movable from a first contracted position, where it supports the stent for insertion, to a second expanded position, where the stent is expanded for fixation, by virtue of relative movement between said inner and outer elongated members;
said relative movement is longitudinal;
said flexible member has at least one opening thereon to permit perfusion of fluids therethrough adjacent the stent while it is being expanded by said flexible member;
said inner and outer elongated members forming an annulus therebetween which is in flow communication with said opening in said flexible member for allowing perfusion during expansion of said flexible member;

said flexible member comprises a generally tubular structure with an undulating wall;

said contracted position defined by a small profile of said undulating wall;

said expanded position results from allowing the profile of said undulating wall to increase to expand the stent; and said undulating wall further comprises an undulation which has a larger profile than said other undulations which comprise said wall, in both the contracted and expanded positions of said wall, to reduce longitudinal shifting of the stent as said wall is expanded.

19. The system of claim 18, wherein:

said outer elongated member is reinforced for column strength against a compressive applied force which results from said relative longitudinal movement.

20. The system of claim 19, wherein:

said reinforcement comprises a wound spring extending for at least a portion of the length of said outer elongated member.

21. The system of claim 20, wherein:

said inner elongated member has a tubular structure to facilitate passing it over a guidewire.

22. A stent delivery system, comprising:

an inner elongated member;

an outer elongated member mounted over and movable with respect to said inner elongated member;

a flexible member connected to said inner elongated member and said outer elongated member;

said flexible member movable from a first contracted position, where it supports the stent for insertion, to a second expanded position, where the stent is expanded for fixation, by virtue of relative movement between said inner and outer elongated members; and said flexible member comprising a travel stop to resist longitudinal movement of said stent by abutting said stent as said flexible member is moved from its said first position to its said second position.

23. A stent delivery system, comprising:

an inner elongated member;

an outer elongated member mounted over and movable with respect to said inner elongated member;

a flexible member connected to said inner elongated member and said outer elongated member;

said flexible member movable from a first contracted position, where it supports the stent for insertion, to a second expanded position, where the stent is expanded for fixation, by virtue of relative movement between said inner and outer elongated members;

said flexible member comprises a generally tubular structure with an undulating wall further comprising at least two reverse bends; and said contracted position defined by a small profile of said reverse bends and said expanded position defined by at least one of said reverse bends moving radially away from another said reverse bend.

* * * * *